United States Patent
Reimer et al.

(10) Patent No.: US 9,480,399 B2
(45) Date of Patent: Nov. 1, 2016

(54) ILLUMINATION DEVICE FOR AN OPTICAL VIEWING APPARATUS

(71) Applicant: Carl Zeiss Meditec AG, Jena (DE)

(72) Inventors: Peter Reimer, Ellwangen (DE); Daniel Kolster, Oberkochen (DE); Franz Merz, Aalen (DE); Stefan Meinkuss, Nattheim (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 14/752,621

(22) Filed: Jun. 26, 2015

(65) Prior Publication Data

US 2015/0374235 A1 Dec. 31, 2015

(30) Foreign Application Priority Data

Jun. 26, 2014 (DE) .................. 10 2014 212 371

(51) Int. Cl.
| | |
|---|---|
| A61B 3/10 | (2006.01) |
| A61B 3/14 | (2006.01) |
| G02B 21/08 | (2006.01) |
| G02B 21/12 | (2006.01) |
| A61B 3/13 | (2006.01) |
| G02B 5/00 | (2006.01) |

(52) U.S. Cl.
CPC . *A61B 3/14* (2013.01); *A61B 3/13* (2013.01); *G02B 5/005* (2013.01); *G02B 21/082* (2013.01); *G02B 21/125* (2013.01)

(58) Field of Classification Search
CPC ........ A61B 3/14; A61B 3/10; A61B 3/1035; A61B 3/107; A61B 3/12
USPC ................ 351/214, 221, 246, 206, 205, 200
See application file for complete search history.

(56) References Cited

U.S. PATENT DOCUMENTS

| | | | |
|---|---|---|---|
| 7,307,785 B2 | 12/2007 | Obrebski et al. | |
| 7,518,149 B2 | 4/2009 | Maaskant et al. | |
| 8,864,311 B2 | 10/2014 | Merz et al. | |
| 2009/0109401 A1* | 4/2009 | Van Heugten | ....... A61B 3/1015 351/221 |
| 2010/0302630 A1 | 12/2010 | Paulus | |

(Continued)

FOREIGN PATENT DOCUMENTS

| | | |
|---|---|---|
| DE | 198 56 847 A1 | 6/1999 |
| DE | 10 2012 217 967 A1 | 4/2014 |
| JP | 8-68942 A | 3/1996 |

OTHER PUBLICATIONS

English translation of the Office action of the German Patent Office dated Mar. 4, 2015 in German patent application 10 2014 212 371.2 on which the claim of priority is based.

(Continued)

*Primary Examiner* — Hung Dang
(74) *Attorney, Agent, or Firm* — Walter Ottesen, P.A.

(57) ABSTRACT

An illumination device for an optical viewing apparatus defines an illumination beam path and includes an illumination light source having mutually independently controllable individual light sources arranged in a first plane in a two-dimensional array. The illumination device defines an illumination beam path and includes illumination optics defining an optical axis. The illumination optics form a second plane conjugated with respect to the first plane. A diaphragm unit is arranged in the second plane. The diaphragm unit has a plurality of apertures and the apertures are assigned to corresponding ones of the individual light sources.

14 Claims, 9 Drawing Sheets

(56) References Cited

U.S. PATENT DOCUMENTS

2012/0057013 A1 3/2012 Ishiwata
2012/0268717 A1* 10/2012 Zhou .................... A61B 3/1015
351/221

OTHER PUBLICATIONS

English translation and search report of the European Patent Office dated Nov. 19, 2015 in corresponding European patent application 15172224.6-1562.

* cited by examiner

ILLUMINATION DEVICE FOR AN OPTICAL VIEWING APPARATUS

CROSS REFERENCE TO RELATED APPLICATION

This application claims priority of German patent application no. 10 2014 212 371.2, filed Jun. 26, 2014, the entire content of which is incorporated herein by reference.

FIELD OF THE INVENTION

The invention relates to an illumination device for an optical viewing apparatus, including an illumination light source having mutually independently controllable individual light sources arranged in a first plane in a two-dimensional array, and an illumination beam path having an illumination optical unit and an optical axis. A plane conjugate with respect to the first plane is formed by the illumination optical unit.

BACKGROUND OF THE INVENTION

U.S. Pat. No. 8,864,311 discloses an illumination device including a light source formed from an arrangement of a plurality of switchable tiny light sources.

What is disadvantageous about the illumination device is that, for different illumination variants, an optimum illumination quality is not achievable in every case. When a rigid diaphragm is introduced into the illumination beam path, the diaphragm aperture is usually adapted to the maximum size of the light source in order to achieve a sharp imaging of the light source in an object region to be illuminated. When the size of the light source is reduced, an imaging of the light source, in particular of the edges of the light source, in the object region to be illuminated is then less sharp. Possible image aberrations of an illumination optical unit can have a more pronounced effect. Stray light or reflex light arising through the illumination optical unit or through mounting edges of optical elements is imaged into the object region. The illumination quality becomes poorer overall.

When a variable diaphragm is used, the size of a diaphragm aperture can be adapted to the size of the illumination light source. However, the outlay for a variable diaphragm aperture and the control thereof is high. The use of transmissive diaphragms, for example liquid crystal displays, is technically complex and results in losses of light. This is disadvantageous in the case of small light sources having limited light power.

SUMMARY OF THE INVENTION

Therefore, it is an object of the invention to provide an improved illumination device for an optical viewing apparatus and a method for operating it with which a high illumination quality is achievable for different illumination variants.

The illumination device of the invention is for an optical viewing apparatus. The illumination device defines an illumination beam path and includes: an illumination light source having mutually independently controllable individual light sources arranged in a two-dimensional array in a first plane; illumination optics defining an optical axis; the illumination optics forming a second plane conjugated with respect to the first plane; a diaphragm unit arranged in the second plane; the diaphragm unit having a plurality of apertures; and, the apertures being assigned to corresponding ones of the individual light sources.

According to the invention, the illumination device for an optical viewing apparatus includes a diaphragm device arranged in the plane conjugate with respect to the first plane. The diaphragm device has a number of diaphragm apertures, wherein each diaphragm aperture is assigned to an individual light source.

The illumination light source includes mutually independently controllable individual light sources arranged in an array in a first plane. The arrangement of the individual light sources in an array enables a compact construction of the illumination light source. By virtue of a mutually independent control of the individual light sources, different illumination variants can be set very rapidly. The array of the independently controllable individual light sources is imaged by an illumination optical unit into a plane which is conjugate with respect to the first plane and in which a diaphragm device is arranged. The diaphragm device has a number of diaphragm apertures, wherein an individual aperture is assigned to each individual light source. Consequently, a high imaging quality in an object plane can be achieved for each individual light source. Each controllable individual light source can be imaged with a sharply delimited edge into an object plane. Possible image aberrations of the illumination optical unit have only a minor effect, such that a cost-effective illumination optical unit can advantageously be used. Stray light or reflex light arising through the illumination optical unit or through mounting edges of optical elements is advantageously masked out or significantly reduced by the diaphragm device. The illumination quality is very high for every illumination variant.

By virtue of the individual guiding of the individual light sources, different illumination variants can be successively provided very rapidly in which the individual light sources are switched on/off individually or in combination or are driven individually in terms of brightness. The illumination variants are thus settable differently in terms of shape, size and brightness. The illumination light can advantageously be adapted to changing application situations by virtue of the individually controllable individual light sources.

In one embodiment of the invention, the size and shape of the apertures are adapted to images of the individual light sources in the conjugate plane. A first principal plane H and a second principal plane H' are defined by the illumination optical unit. A first distance (s) is formed as distance between the first principal plane H and the first plane and a second distance s' is formed as distance between the second principal plane H' and the plane conjugate with respect to the first plane, wherein the following relationship is fulfilled for a magnification scale:

$$1 \leq \left|\frac{s'}{s}\right| \leq 4, \quad \text{preferably} \quad 1.3 \leq \left|\frac{s'}{s}\right| \leq 3,$$
$$\text{particularly preferably} \quad 1.6 \leq \left|\frac{s'}{s}\right| \leq 2.3.$$

The individual light sources can be very small. By virtue of the adaptation of the apertures in terms of size and shape to images of the individual light sources in the conjugate plane on a specific magnification scale, the diaphragm device can be produced more simply and more cost-effectively. Manufacturing tolerances of the apertures have a reduced effect. In the case of the magnification scale mentioned, a very good imaging performance is achievable in conjunction with very good luminance. This results in a very high illumination quality in conjunction with very good ergonomics.

In one embodiment of the invention, the illumination light source has at least four individual light sources.

At least three different illumination variants are settable by at least four individual light sources.

In one embodiment of the invention, not all positions in the two-dimensional array are occupied by individual light sources.

An individual light source is assigned to each aperture. If not all positions in the two-dimensional array are occupied by individual light sources, the respectively assigned aperture can advantageously be dispensed with. The diaphragm can be produced more expediently. No stray light is caused by the unoccupied position. A possible evolution of heat in the illumination unit is smaller.

In one embodiment of the invention, the individual light sources are embodied in square, rectangular or round fashion.

The embodiment of the individual light sources in square, rectangular or round shape enables simple production of the apertures that are adapted in terms of size and shape to the individual light sources. Manufacture of an array including individual light sources having the abovementioned shape is cost-effective.

In one embodiment of the invention, the individual light sources arranged in the two-dimensional array are arranged in cruciform fashion.

Illumination in two axial directions is thus possible. In the case of four individual light sources, for example, an individual light source can be positioned on each limb of the cruciform arrangement.

In one embodiment of the invention, the individual light sources arranged in the two-dimensional array are arranged in at least two rows and at least two columns.

In the case of this arrangement, diverse illumination variants are settable. By virtue of an independent control of individual light sources individually or in combination, in columns or in rows, illumination angles and brightnesses are variable.

In one embodiment of the invention, a control device is present, by which the brightness of each individual light source is controllable by voltage and/or current control or by a pulse width modulation with freely settable pulse ratios.

The illumination variants are settable by the specific control or regulation of specific individual light sources at specific positions of the two-dimensional array. The brightness of the illumination light can be increased by one or a plurality of individual light sources being switched on. Advantageously, the brightness of the individual light sources can additionally be defined by control of the voltage and/or of the current. In order to be able to set the individual light sources in a wide brightness range in very fine gradations, control can advantageously be effected by pulse width modulation with freely settable pulse ratios.

In one embodiment of the invention, the control device is embodied in such a way that one or a plurality of individual light sources are drivable with lower or higher intensity or with a different frequency pattern than the rest of the individual light sources, such that the one or the plurality of individual light sources form a fixation light.

A fixation light is a light spot fixed on by a patient with the latter's eye during an operation. The position of the patient's eye is thus situated in a defined and stable position. The fixation light can be offered to the patient's eye by an individually drivable individual light source or a plurality of individual light sources. No additional optical unit is required. The fixation light is sharply imaged onto the retina of a patient's eye with normal vision by the illumination optical unit. Advantageously, already existing components of a control device for controlling the individual light sources can likewise be used for controlling the fixation light. A fixation light can thus be realized in a space-saving and cost-effective manner.

In one embodiment of the invention, one or a plurality of individual light sources are configured for emitting light having a different wavelength than the rest of the individual light sources.

If an individual light source differs in terms of the emitted wavelength, or in terms of the color, from the individual light sources used as illumination light, it is discernible very rapidly and easily to an eye to be examined and can advantageously form a fixation light.

In accordance with a second aspect of the invention, a surgical microscope including an illumination device described above is provided.

In the case of the embodiment of a surgical microscope including an illumination device of the type described above, illumination variants can advantageously be realized in various ways. Typically, the illumination light is coupled into a first monoscopic or stereoscopic viewing beam path. Coupling into a second monoscopic or stereoscopic viewing beam path is also conceivable. As a result of the arrangement of the individual light sources in a two-dimensional array, different illumination angles can be achieved by selective control of the individual light sources. A red reflex illumination can advantageously be formed by coaxial coupling of an illumination beam path into a viewing beam path.

In one embodiment of the invention, a camera is arranged in a viewing beam path, the camera being connected to a control device. The control device is configured for detecting a red reflex of an eye and for driving the individual light sources arranged in the two-dimensional array in a manner dependent on a dimension figure for the red reflex.

The individual light sources can thus be controlled automatically depending on an illumination situation of an eye to be observed. The images from a camera are evaluatable by the control device with regard to a red reflex of the eye. Depending on the formation of the red reflex, the controller determines a dimension figure. An illumination variant can be set automatically depending on the calculated dimension figure.

In accordance with a third aspect of the invention, a method for automatically switching an illumination variant with a surgical microscope is provided, characterized by the following steps:

recording an image of an eye via the camera arranged in the viewing beam path;

evaluating the image from the camera via the control device;

detecting a red reflex of the eye via the control device;

determining a dimension figure for the red reflex;

driving the individual light sources arranged in a two-dimensional array in a manner dependent on the dimension figure for the red reflex.

A red reflex in an eye can be detected by the evaluation of the images from a camera arranged in the viewing beam path. Depending on the formation of the red reflex, the controller determines a dimension figure. Automatic driving of a single or a plurality of individual light sources is carried out depending on the dimension figure. It is thus possible to provide an automated setting or switching of an illumination variant for the surgical microscope.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
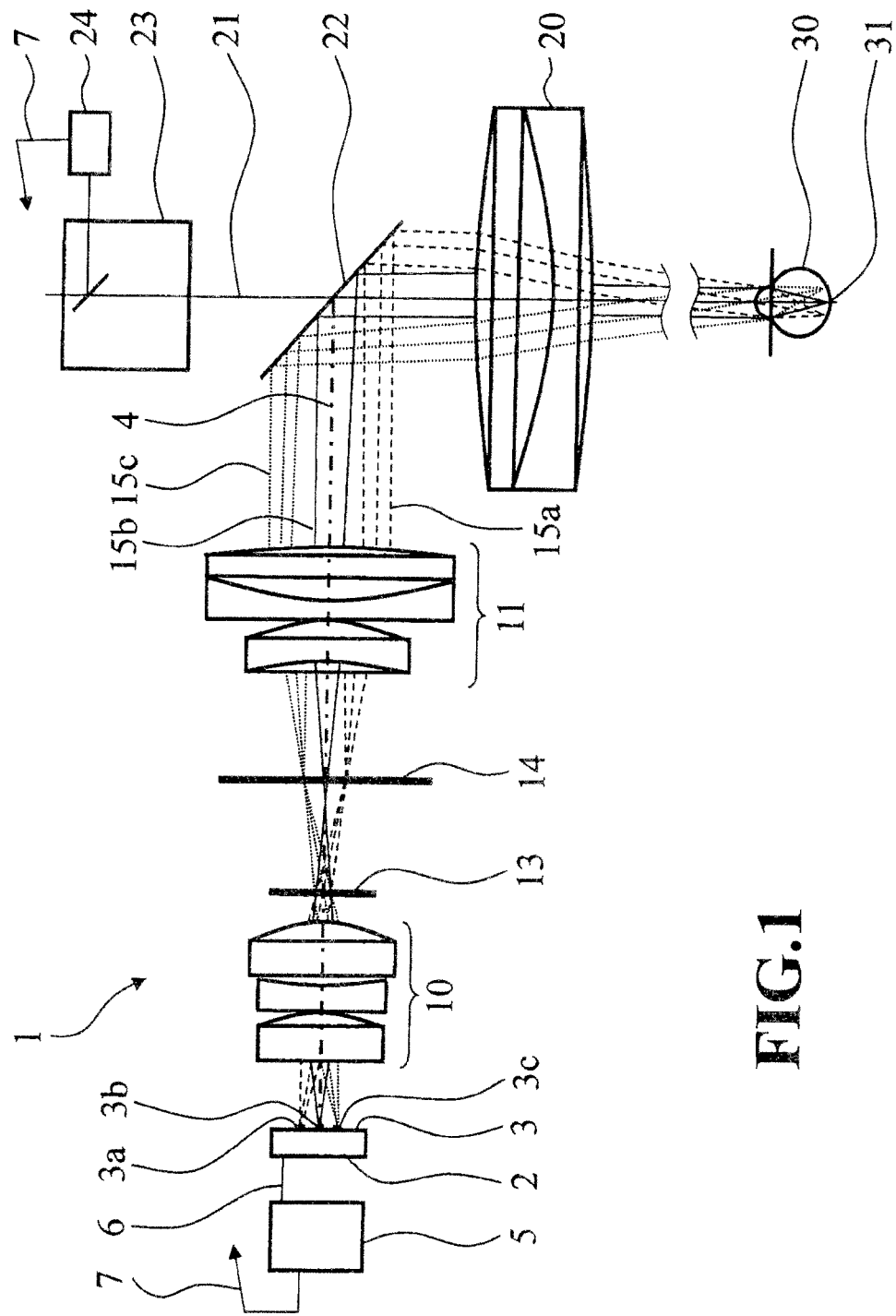
FIG. 1 shows a first embodiment of an illumination device according to the invention with a surgical microscope.

FIG. 1 shows a first embodiment of an illumination device 1 according to the invention with a surgical microscope. The surgical microscope is embodied as a stereomicroscope.

The illumination device 1 includes a light source unit 2, a first lens group 10, a luminous field stop 13, a diaphragm device 14 and a second lens group 11, which are arranged along an optical axis 4. The light source unit 2 includes a two-dimensional individual light source array 3 including a first individual light source 3a, a second individual light source 3b and a third individual light source 3c. The individual light source array 3 includes further individual light sources (not illustrated). The individual light source array 3 is arranged in a first plane perpendicular to the optical axis 4. The second individual light source 3b is arranged on the optical axis 4. The light source unit 2 is connected to a control device 5 via a line 6.

The illumination light beams generated by the individual light source array 3 are led through the first lens group 10, the luminous field stop 13, the diaphragm device 14 and the second lens group 11 and are coupled into a viewing beam path of the surgical microscope via a deflection element 22, for example a beam splitter. The surgical microscope includes a main objective 20 and an observation optical unit 23, which is merely indicated schematically. A stereoscopic viewing beam path for a first observer is embodied parallel to an optical axis 21. In this embodiment, the stereoscopic viewing beam path is arranged with a left and a right viewing beam path perpendicular to the illustrated plane of the drawing, such that the two optical axes of the left and right viewing beam paths are congruent in this view.

A camera 24 is coupled to one viewing beam path via a beam splitter, the camera being connected to the control device 5 via a line 7. An input-output unit (not illustrated) can be connected to the control device.

The first lens group 10 can include an individual lens or a plurality of lens elements. The first lens group 10 forms a collector optical unit. The first lens group 10 images the individual light source array 3 into a plane which is conjugate with respect to the first plane and in which the diaphragm device 14 is arranged. The diaphragm device 14 has a number of apertures, wherein each aperture is assigned to an individual light source. The apertures of the diaphragm device 14 in this case form a magnified image of the individual light source array 3. The diaphragm device 14 is arranged in a manner rotated by 180° relative to the optical axis 4 with respect to the individual light source array 3.

The second lens group 11 together with the main objective 20 forms a condenser lens group. The second lens group 11 can include an individual lens or a number of lens elements. The illumination light is led below the main objective 20 in a parallel beam and is imaged toward infinity. The illumination light impinges on an object to be observed, an eye 30. In the eye 30, the light source image of the individual light sources is imaged on a fundus 31.

From the second individual light source 3b, a second illumination beam 15b runs parallel to the optical axis 4 and is coupled coaxially into the left viewing beam path. The light from the second individual light source 3b generates an illumination spot on the fundus 31 of the eye 30. An observer can perceive the light backscattered from the fundus 31 as red reflex when looking through the surgical microscope.

If the left viewing beam path is projected onto the fundus, it forms an approximately round cross section on the fundus. The illumination spot generated by the second individual light source 3b lies within the cross section.

A first illumination beam 15a running from the first individual light source 3a is led to the eye 30 at a small angle of approximately −2° with respect to the optical axis of one viewing beam path and forms a −2° illumination.

By contrast, a third illumination beam 15c running from the third individual light source 3c is led to the eye 30 at a small angle of approximately 2° with respect to the optical axis of one viewing beam path and forms a 2° illumination with respect to the opposite side of the optical axis.

The explanations described above apply both to a left and to a right viewing beam path. For the right viewing beam path the individual light source array 3 includes three further individual light sources situated behind the individual light sources (3a, 3b, 3c) in the plane of the drawing.

The light source unit 2 includes the individual light source array 3, wherein each individual light source is formed from an LED or an OLED. It is also conceivable for the individual light sources to include optical fibers and for the individual light sources to be formed from the fiber ends of the optical fibers. A very compact configuration of the individual light sources is thus achievable. In the case where the individual light sources are embodied as LEDs or OLEDs, the individual light sources can be electrically controlled very rapidly and simply. In the case of the configuration as exit end of optical fibers, no heat is generated in the plane of the two-dimensional array and heat-dissipating measures can be dispensed with at this location. The individual light source array 3 can also include a combination of LEDs, OLEDs and optical fibers. It is also conceivable for the individual light sources to be formed by lasers or excited converters. The individual light sources can have a square, rectangular or round emission surface.

The control device 5 is configured to switch the first individual light sources 3a, the second individual light source 3b, the third individual light source 3c and all further individual light sources (not illustrated) of the individual light source array on and off independently of one another. Furthermore, the brightness of all the individual light sources can be set by control of the voltage or current of the individual light sources. Alternatively, the brightness is controllable by a pulse width modulation with freely settable pulse ratios. An electronic brightness setting of the individual light sources has the advantage that no movable parts, such as filters, for example, have to be introduced into the illumination beam path.

Figure 2:
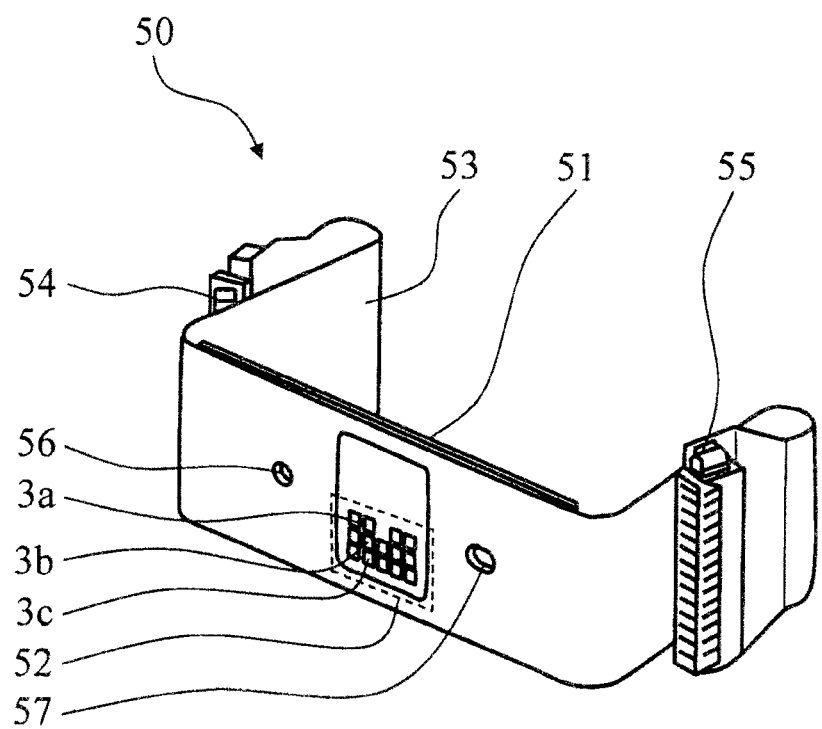
FIG. 2 shows one embodiment of a light source unit having an individual light source array.

FIG. 2 shows one embodiment of a light source unit 50 having an individual light source array. The individual light source array is embodied as an LED matrix 52 having fourteen LED individual light sources. The LED individual light sources are arranged as SMD LEDs on a circuit board 51 and can each be driven individually. The anodes of all the individual light sources can be connected, while the emitters are led in each case via an individual line to the control device 5. However, it is also conceivable for the LED individual light sources to be electrically connected in a grid arrangement and to be driven via multiplex electronics. The multiplex electronics can be arranged on the circuit board 51 or integrated in the control unit 5. The circuit board 51 has a first cutout 56 and a second cutout 57 for a respective mechanical fixing element. The circuit board is connected to a ribbon cable 53. The ribbon cable has a first plug connector 54 and a second plug connector 55, with which the LED matrix 52 can be connected to the control device 5.

Three LED individual light sources arranged in a column of the LED matrix 52 can form the first individual light source 3a, second individual light source 3b and third individual light source 3c illustrated in FIG. 1.

Figure 3:
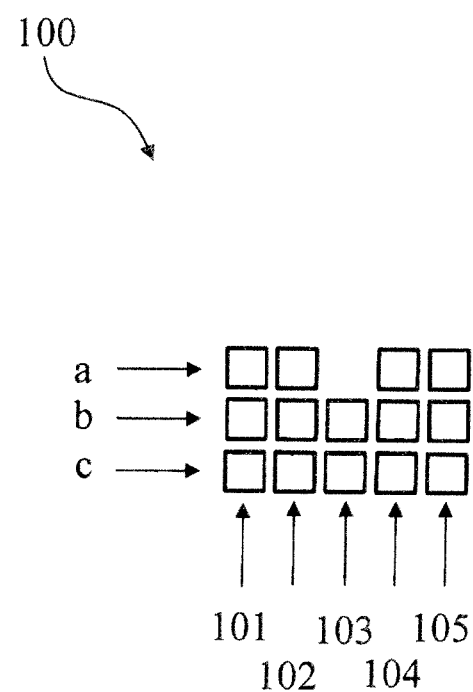
FIG. 3 shows the individual light source array in accordance with FIG. 2 in a schematic illustration.

FIG. 3 shows the individual light source array in accordance with FIG. 2 in a schematic illustration. The arrangement of the individual light sources corresponds to the LED matrix 52. The individual light sources of an individual light source array 100 are arranged in three rows and five columns. The rows are designated by lower hyphen-case letters and the columns are designated by numerals. The individual light source array has a total of 14 individual light sources, wherein four individual light sources are arranged in a first row (a), and in each case five individual light sources are arranged in a second row (b) and a third row (c). A first column 101, a second column 102, a fourth column 104 and a fifth column 105 in each case have three individual light sources. Only two individual light sources are arranged in a third column 103.

The position of an individual light source in the individual light source array can be unambiguously defined by the combination of the numeral of the respective column and the letter of the respective row.

If an individual light source at a specific position is not switched on, then the individual light source can be dispensed with in the array. In this embodiment, the individual light source at the position 103a (column 103, row a) is dispensed with in order to avoid possible reflections of an individual light source at this position from the main objective into a viewing beam path. A reflection stop that is otherwise necessary is thus obviated. The omission or the deactivation of this individual light source reduces stray light and a possible evolution of heat in the illumination unit.

Figure 4:
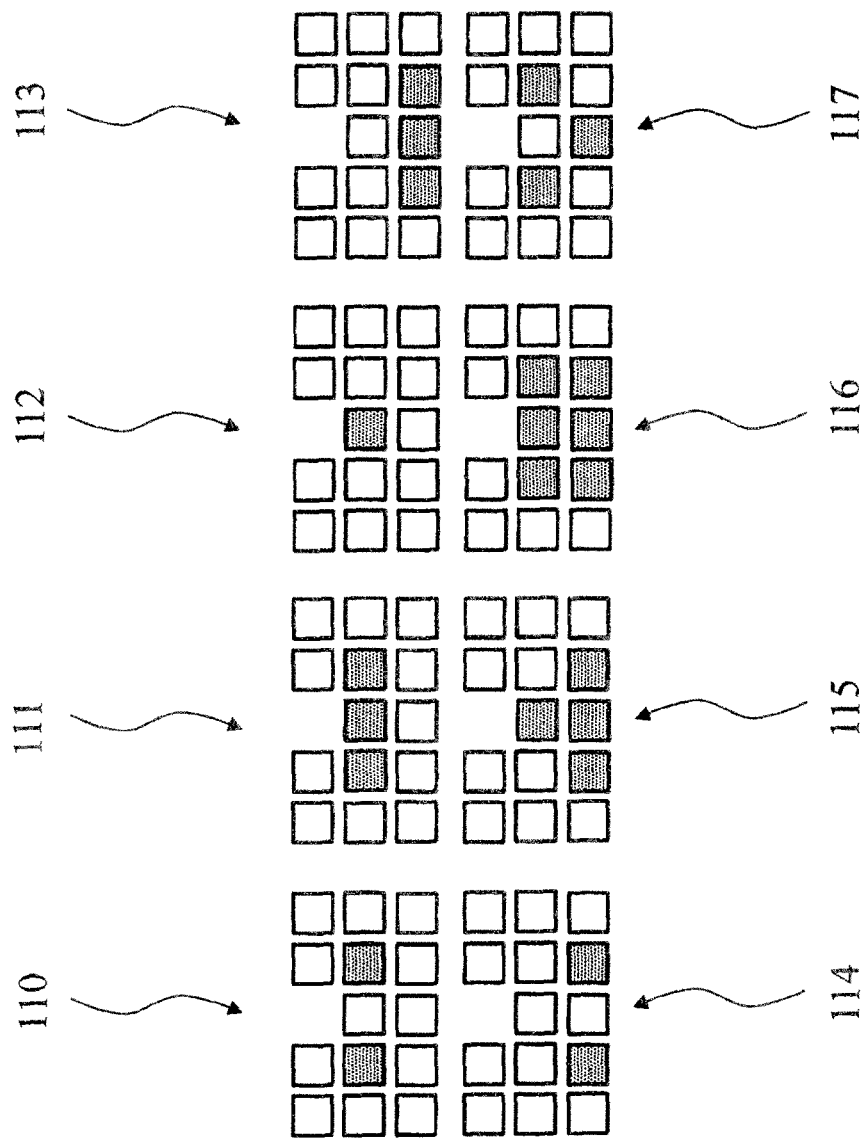
FIG. 4 shows eight different illumination variants of the individual light source array in accordance with FIG. 3.

FIG. 4 shows eight different illumination variants of the individual light source array from FIG. 3. By virtue of the separate drivability of each single individual light source, the illumination angle and also the diameter and the brightness of the illumination can be adapted individually to the respective situation during the observation of the eye 30 or the anatomical conditions of the eye 30.

In a first illumination variant 110, two individual light sources at the positions 102b and 104b are switched on. The light from these individual light sources is in each case coupled coaxially into the left and right beam paths of the viewing device. The illumination spots of the individual light sources are smaller than the imagings of the respective left and right viewing beam paths that are projected onto the fundus. This illumination variant 110 has the effect of a stereo-coaxial illumination. The observer can perceive a very high-contrast and homogeneous red reflex image through the viewing device.

In a second illumination variant 111, in addition to the two individual light sources from the illumination variant 110, an intervening individual light source at the position 103b is also switched on. The additional light source brings about a brightening of the red reflex. The contrast of the red reflex is good, but somewhat lower than in the first illumination variant 110.

In a third illumination variant 112, only the central individual light source at the position 103b is switched on. An observer can perceive a high-contrast image with a good depth effect, but at low brightness. Only little light is input into the eye.

In a fourth illumination variant 113, in the third row (c) the three central individual light sources at the positions (102c, 103c, 104c) are activated. It is thus possible to obtain a bright red reflex as in the case of a 2° illumination. The 2° illumination brings about a large depth effect. Contrast and homogeneity are acceptable. The additionally switched-on individual light source at the position 103c brings about a brightening of the image.

In a fifth illumination variant 114, in the third row (c) only the two individual light sources at the positions 102c and 104c are switched on. It is thus possible to obtain a good red reflex as in the case of a 2° illumination. The 2° illumination brings about a large depth effect in conjunction with acceptable homogeneity. The image impression is somewhat darker than in the fourth illumination variant 113, but in return the contrast is better.

In a sixth illumination variant 115, a total of four individual light sources emit light, at the positions (103b, 102c, 103c, 104c). This illumination variant has the effect of a 2° illumination like the fourth illumination variant 113. The additionally activated individual light source at the positions 103b results in a brightening of the image, but with somewhat reduced contrast.

In a seventh illumination variant 116, a total of six individual light sources are activated, at the positions (102b, 103b, 104b, 102c, 103c, 104c). This combination constituted a combination of the second illumination variant 111 and the fourth illumination variant 113. The result is a very bright image. However, the contrast is low.

In an eighth illumination variant 117, three individual light sources emit light. The individual light source at the position 103c is switched on in addition to the two individual light sources at the positions 102b and 104b from the illumination variant 110. This illumination variant has the effect of a stereo-coaxial illumination in conjunction with very good contrast and good homogeneity and in conjunction with an improved depth effect.

An application of the illumination variants described is of importance for example in eye surgery, in particular cataract surgery. In the first phase of a cataract operation, a high contrast is desirable in order that the course of a capsulorhexis can be controlled well. The first illumination variant 110 of a stereo-coaxial illumination is advantageously activated, which brings about a small fundus spot. The observer can perceive a very high-contrast and homogeneous red reflex image through the viewing device. The lens capsule of the eye can be discerned very well by virtue of the high contrast.

In a second phase, so-called hydrodissection and the removal of the lens core by phacoemulsification, the structure of the eye lens is greatly altered. The lens material causes the illumination light to be scattered, such that only little illumination light reaches the fundus. The red reflex becomes weaker or vanishes entirely. In this second phase, the brightness of the illumination is to be increased. In addition, a larger fundus spot is advantageous. A greater depth of field can be brought about by a 2° illumination. A 2° illumination is formed by the fifth illumination variant 114. In order to increase the brightness, further individual light sources can be switched on. The fourth illumination variant 113, in which a further individual light source is switched on, is appropriate. If the brightness is still insufficient, two individual light sources in the sixth illumination variant 115 or four individual light sources in the seventh illumination variant 116 can additionally be activated.

In a third phase, the final phase of the phacoemulsification, the last residues of the eye lens are removed. Since the cloudy and scattering lens particles are removed from the eye to the greatest possible extent, the brightness of the illumination can be reduced. A high contrast is demanded, which is achieved in the case of a coaxial illumination with small fundus spots. The first illumination variant 110 or the second illumination variant 111 is activated.

The illumination variant optimized for the respective use phase can be set in this way. The observer can change between a coaxial illumination or an oblique illumination, or 2° illumination, or combine both types of illumination. The size of the fundus spots, the illumination angle and the brightness can be optimally adapted here to the respective situation.

The different illumination variants are stored in the control device 5. The observer can switch over the illumination variants via a switching element (not illustrated). It is conceivable for the control device to have a configuration menu in which the different illumination variants are presettable, which can then be activated sequentially via the switching element in the operating mode. The switching element can be part of a handle, a foot-operated switching console, an input-output unit or some other known input element.

It is also conceivable for the control device 5 to include an image processing unit suitable for evaluating the image data from a camera 24 arranged in the viewing beam path. The image processing can be configured in such a way that it automatically detects the red reflex and determines a dimensioned figure, for example a parameter value of the red reflex. A dimension figure or a parameter value can be determinable via the brightness, size, shape or contrast value of the red reflex.

The control device 5 can automatically set an illumination variant depending on the dimensioned figure. Provision can be made for the brightness to be immediately increased if the red reflex suddenly vanishes, by at least one further individual light source being switched on. It is also conceivable for the seventh illumination variant 116 to be set automatically in this case.

Figure 5:
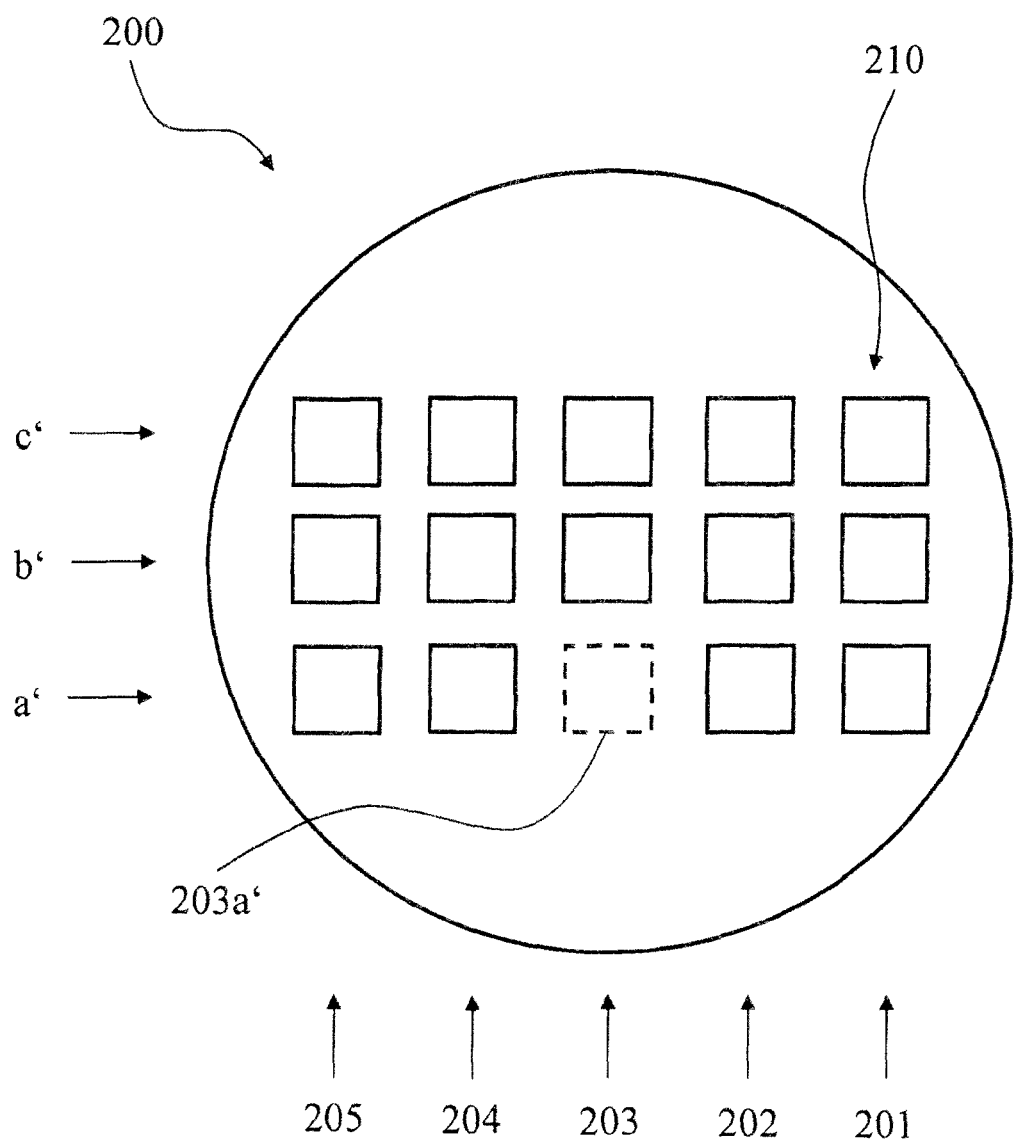
FIG. 5 shows one embodiment of a diaphragm device.

FIG. 5 shows one embodiment of a diaphragm device 200. In this embodiment, the diaphragm device 200 is embodied in a circular fashion. The diaphragm device 200 has apertures 210 corresponding to a magnified image of the individual light source array of the light source unit. FIG. 2 shows an embodiment of the light source unit as an LED matrix 52 having individual light sources embodied in square fashion. The apertures 210 are therefore likewise embodied in square fashion. The aperture device 200 has apertures 210 in three rows and five columns. The apertures are arranged in a first row a', a second row b' and a third row c', and a first column 201, a second column 202, a third column 203, a fourth column 204 and a fifth column 205. The position of an aperture 210 can be unambiguously defined by the combination of the numeral of the respective column and the letter of the respective row.

In accordance with FIG. 1, the diaphragm device 200 is arranged in a manner rotated by 180° relative to the individual light source array in the beam path along the optical axis. The light from the individual light source at the position 102c thus passes through the aperture at the position 202c'. The aperture at the position 203a' is optional. In the case of the individual light source array in accordance with FIG. 2 and FIG. 3, the individual light source at the position 103a has been dispensed with for reasons of avoiding reflection. Therefore, an aperture at the position 203a' is not necessary in this case. With the use of a different light source array having an individual light source at the position 103a, the diaphragm device 200 also has an aperture 210 at the position 203a'.

The diaphragm device 200 can be produced from very thin sheet metal. The square apertures 210 can be produced for example by stamping, laser cutting, water jet cutting or etching.

The apertures 210 can also be embodied in round fashion. In this case, the midpoints of the round apertures correspond to the midpoints of the individual light sources.

Figure 6:
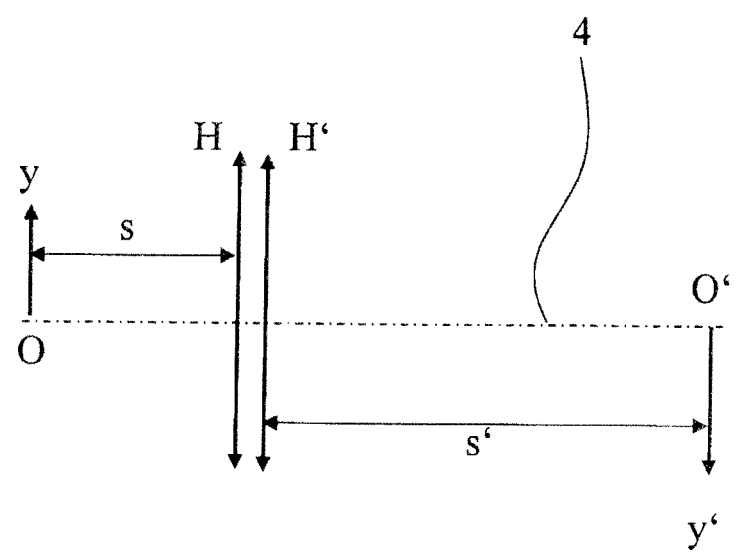
FIG. 6 shows a schematic illustration of a beam path between the light source unit and the diaphragm device in accordance with FIG. 1.

FIG. 6 shows a schematic illustration of a beam path between the light source unit 2 and the diaphragm device 14 in accordance with FIG. 1.

The optical axis 4 of the illumination optical unit is depicted as a dash-dotted line. Perpendicular to the optical axis 4, a first principal plane H is situated as reference plane for focal lengths or distance indications in the object space and a second principal plane H' is situated as reference plane for the image space. The two principal planes (H, H') allow the effect of the first lens group 10 to be described with the equation valid for a thin lens. The first principal plane H and the second principal plane H' are both defined perpendicular to the optical axis of the lens system and thus run parallel to one another. The two principal planes (H, H') replace the first lens group 10.

A first plane is formed by the individual light source array arranged perpendicularly to the optical axis 4. An object O lies in the first plane. The object point O is defined by an individual light source of the individual light source array and has an object size (y). The first distance (s) is the distance between the first principal plane H and the first plane.

The object point O is imaged by the first lens group 10 to form an image point O'. The image point O' lies in a plane conjugate with respect to the first plane. The diaphragm device 14 is arranged in this conjugate plane. The second distance s' is the distance between the second principal plane H' and the plane conjugate with respect to the first plane with the image point O'. The object size y of an individual light source is represented on a magnified scale as image size y' in the conjugate plane. An aperture of the diaphragm device 14, or the entire diaphragm device 14, which corresponds to an image of the individual light source array, is therefore implemented on a magnified scale. The following relationship holds true for the magnification scale:

$$1 \le \left|\frac{s'}{s}\right| \le 4, \quad \text{preferably} \quad 1.3 \le \left|\frac{s'}{s}\right| \le 3,$$

-continued $$\text{particularly preferably} \quad 1.6 \leq \left|\frac{s'}{s}\right| \leq 2.3.$$

Figure 7:
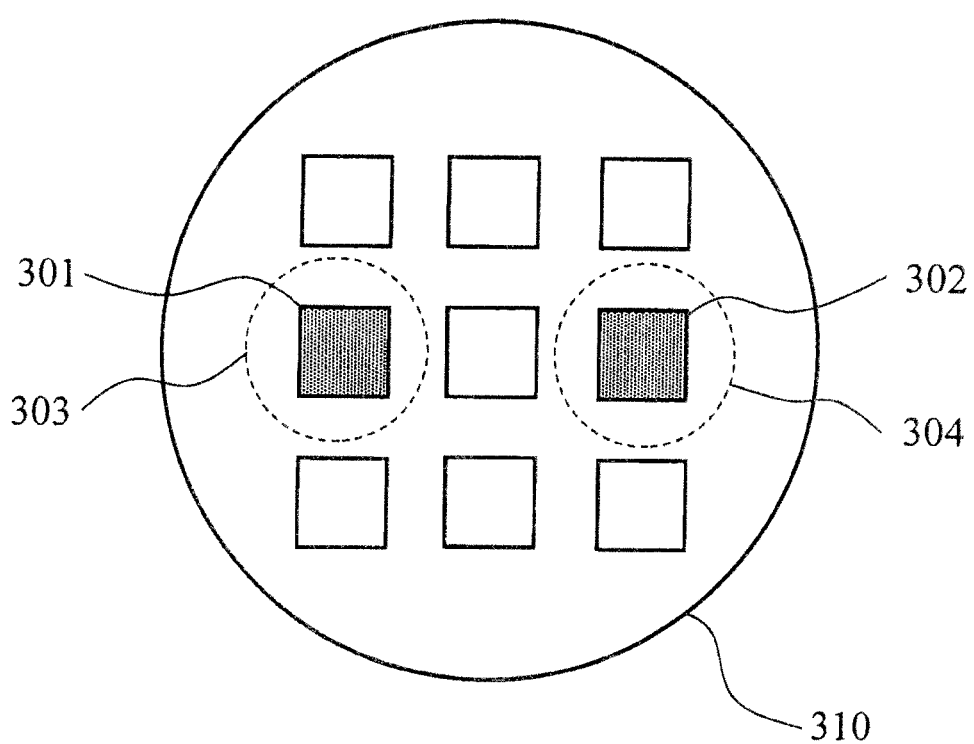
FIG. 7 shows an imaging of the illumination spots on a fundus of an eye for a stereoscopic observer.

FIG. 7 shows an imaging of the illumination spots on a fundus of an eye for a stereoscopic observer. Nine individual light sources of the individual light source array in accordance with FIG. 3 are illustrated in this example. Two individual light sources at the positions 102b and 104b are switched on. The light from the individual light sources is imaged, as illustrated in FIG. 1, through the illumination optical unit and the main objective 20 on the fundus 31 of the eye 30 to be observed. The eye is represented schematically by the circle 310. The imaging of an individual light source on the fundus 31 is designated as illumination spot. The individual light source at the position 102b is coaxially coupled into a first, or left, viewing beam path and forms a first illumination spot 301 on the fundus. The individual light source at the position 104b is coaxially coupled into the second, or right, viewing beam path and forms a second illumination spot 302 on the fundus.

The imagings of the respective first and second viewing beam paths that are projected onto the fundus are designated as observation spots and are illustrated as a dashed line. A first observation spot 303 of the first viewing beam path is larger than the first illumination spot 301 and a second observation spot 304 of the second viewing beam path is larger than the second illumination spot 302. The first illumination spot 301 lies completely within the region of the first observation spot 303. The second illumination spot 302 lies completely within the second observation spot 304. In the case of a first illumination variant 110 in accordance with FIG. 4, a very good contrast of the phase objects is achievable via the small illumination spots (301, 302).

Figure 8:
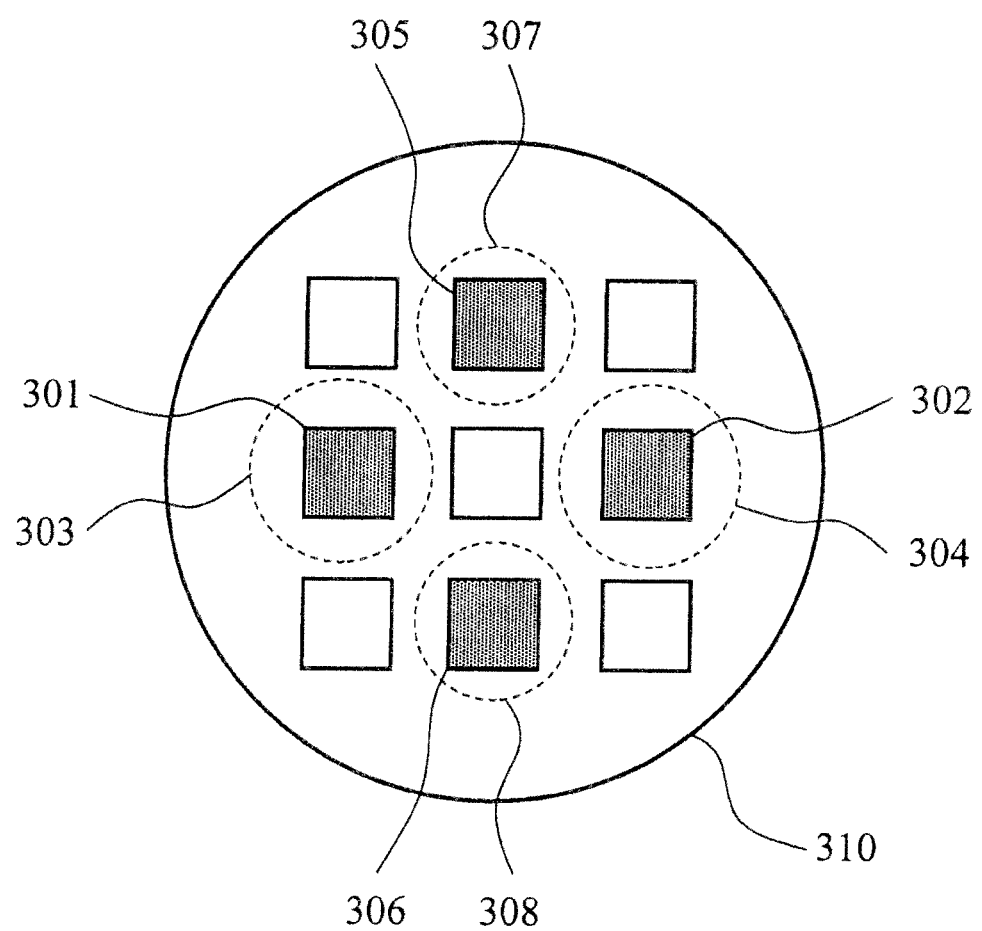
FIG. 8 shows an imaging of the illumination spots on a fundus for two stereoscopic observers; and, FIG. 9 shows an eye aligned with a fixation light.

FIG. 8 shows an imaging of the illumination spots on a fundus for two stereoscopic observers. A second observer sees the fundus in a position offset by 90° relative to the first observer.

As already described in FIG. 7, the imagings of the illumination spots on the fundus and the associated observation spots for a first stereo-coaxial illumination are represented for the first observer.

FIG. 8 differs from the illumination situation in accordance with FIG. 7 in that there is additionally a second stereo-coaxial illumination for a second observer in a 90° position with respect to the first observer. The individual light source at the position 103a is coaxially coupled into the left viewing beam path for the second observer and forms a third illumination spot 305 on the fundus. The individual light source at the position 103c is coaxially coupled into the right viewing beam path for the second observer and forms a fourth illumination spot 306 on the fundus. The third illumination spot lies within a third observation spot 307 for a left viewing beam path of the second observer. The fourth illumination spot 306 lies within a fourth observation spot 308 for a right viewing beam path of the second observer.

Figure 9:
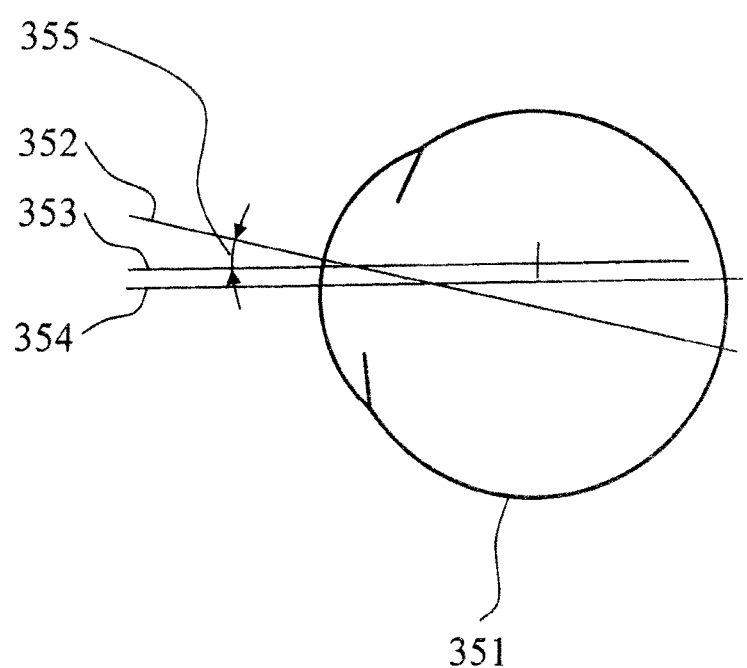

FIG. 9 shows an eye aligned with a fixation light. In the case of the application of a surgical microscope in ophthalmosurgery, for example in the case of cataract surgery or refractive corneal surgery, it is often necessary to align the eye with respect to a viewing beam path or the optical axis of a measuring system. Such measuring systems can be for example a keratoscope or a measuring system for intraoperative refraction measurement. In this case, the axis of vision of an eye to be treated is intended to be aligned with the optical axis of a viewing beam path or of a measuring system.

An eye 351 has an optical axis 352 and an axis 354 of vision, which axes can run differently in the eye 351. Likewise, the axis 354 of vision does not necessarily run through the center of the pupil. The eye 351 can be aligned by the eye 351 being offered a fixation light as fixation point. If the eye is aligned with the fixation light, a fixation line 353 running parallel to the axis 354 of vision is defined. In this case, the fixation line 353 can form an angle 355 relative to the optical axis 352 of the eye 351. In the case of alignment with the fixation point, the eye 351 is situated in a defined position.

If a fixation light as additional light source is arranged on a surgical microscope via a carrier, this disadvantageously influences the free working distance between the main objective of the surgical microscope and the eye.

The fixation light can be embodied by an individual light source of the light source array 3. The fixation light can be arranged for example via the central individual light source at the position 103b as illustrated in the third illumination variant 112 in accordance with FIG. 4. The fixation light lies for example in the center between the left and right viewing beam paths. For this purpose, the central individual light source can be embodied in a different color, for example red. The fixation light does not necessitate a further optical element in the illumination light beam path. An eye with normal vision sees the fixation light sharply. It is also conceivable to arrange additional individual light sources as fixation light between the individual light sources used as illumination light sources.

It is understood that the foregoing description is that of the preferred embodiments of the invention and that various changes and modifications may be made thereto without departing from the spirit and scope of the invention as defined in the appended claims.

LIST OF REFERENCE SIGNS

| | | | |
|---|---|---|---|
| 1 | Illumination device | 55 | Second plug connector |
| 2 | Light source unit | 56 | First cutout |
| 3 | Individual light source array | 57 | Second cutout |
| 3a | First individual light source | 100 | Individual light source array |
| 3b | Second individual light source | | |
| 3c | Third individual light source | 101 | First column |
| 4 | Optical axis of the illumination beam path | 102 | Second column |
| | | 103 | Third column |
| 5 | Control device | 104 | Fourth column |
| 6 | Line | 105 | Fifth column |
| 7 | Line | a | First row |
| 10 | First lens group | b | Second row |
| 11 | Second lens group | c | Third row |
| 13 | Luminous field stop | 110 | First illumination variant |
| 14 | Diaphragm device | | |
| 15a | First illumination beam | 111 | Second illumination variant |
| 15b | Second illumination beam | | |
| 15c | Third illumination beam | 112 | Third illumination variant |
| 20 | Main objective | | |
| 21 | Optical axis of the viewing beam path | 113 | Fourth illumination variant |
| | | | |
| 22 | Deflection element | 114 | Fifth illumination variant |
| 23 | Observation optical unit | | |
| 24 | Camera | 115 | Sixth illumination variant |
| 30 | Eye | | |
| 31 | Fundus | 116 | Seventh illumination variant |
| 50 | Light source unit | | |
| 51 | Circuit board | 117 | Eighth illumination variant |
| 52 | LED matrix | | |
| 53 | Ribbon cable | 200 | Diaphragm device |
| 54 | First plug connector | 201 | First column |

-continued

LIST OF REFERENCE SIGNS

| 210 | Apertures | 202 | Second column |
|---|---|---|---|
| 301 | First illumination spot | 203 | Third column |
| 302 | Second illumination spot | 204 | Fourth column |
| 303 | First observation spot | 205 | Fifth column |
| 304 | Second observation spot | a' | First row |
| 305 | Third illumination spot | b' | Second row |
| 306 | Fourth illumination spot | c' | Third row |
| 307 | Third observation spot | | |
| 308 | Fourth observation spot | | |
| 310 | Circle | | |
| 351 | Eye | | |
| 352 | Optical axis of the eye 351 | | |
| 353 | Fixation line | | |
| 354 | Axis of vision | | |
| 355 | Angle | | |

What is claimed is:

1. An illumination device for an optical viewing apparatus, the illumination device defining an illumination beam path and comprising:
an illumination light source having mutually independently controllable individual light sources arranged in a two-dimensional array in a first plane;
illumination optics defining an optical axis;
said illumination optics forming a second plane conjugated with respect to said first plane;
a diaphragm unit arranged in said second plane;
said diaphragm unit having a plurality of apertures; and,
said apertures being assigned to corresponding ones of said individual light sources;
said apertures have a size and shape adapted to respective images of said individual light sources in said second plane;
said illumination optics define a first main plane (H) and a second main plane (H');
said first main plane (H) and said first plane define a first distance (s) therebetween;
said second main plane (H') and said second plane define a second distance (s') therebetween;
wherein the following relationship is satisfied for a magnification scale:

$1 \leq |s'/s| \leq 4$.

2. The illumination device of claim 1, wherein said relationship for said magnification scale is $$1.3 \leq \left|\frac{s'}{s}\right| \leq 3.$$

3. The illumination device of claim 1, wherein said relationship for said magnification scale is $$1.6 \leq \left|\frac{s'}{s}\right| \leq 2.3.$$

4. The illumination device of claim 1, wherein said illumination light source has at least four of said individual light sources.

5. The illumination device of claim 1, wherein said two-dimensional array defines a plurality of positions with said individual light sources occupying selected ones of said positions.

6. The illumination device of claim 1, wherein said individual light sources are configured in the shape of squares, in the shape of rectangles or round.

7. The illumination device of claim 1, wherein said individual light sources are arranged in the shape of a cross in said two-dimensional array.

8. The illumination device of claim 1, wherein said individual light sources are arranged in at least two rows and in at least two columns in said two-dimensional array.

9. The illumination device of claim 1 further comprising:
a control unit configured to control the brightness of each of said individual light sources via control of at least one of voltage, current and pulsewidth modulation with freely settable pulse ratios.

10. The illumination device of claim 9, wherein:
said control unit is configured such that one or several of said individual light sources is driveable with lesser or greater intensity or with a frequency pattern different than the other ones of said individual light sources so that one or several of said individual light sources form a fixation light.

11. The illumination device of claim 9, wherein at least one of said individual light sources is configured to emit light having a wavelength different than the other ones of said individual light sources.

12. The surgical microscope of claim 1 further comprising:
a control unit;
a camera arranged in said viewing beam path and connected to said control unit; and,
said control unit being configured to detect a red reflex of an eye and to drive said individual light sources arranged in said two-dimensional array in dependence on a dimension figure for said red reflex.

13. A surgical microscope defining a viewing beam path and comprising:
an illumination device defining an illumination beam path and including:
an illumination light source having mutually independently controllable individual light sources arranged in a two-dimensional array in a first plane;
illumination optics defining an optical axis;
said illumination optics forming a second plane conjugated with respect to said first plane;
a diaphragm unit arranged in said second plane; said diaphragm unit having a plurality of apertures; and, said apertures being assigned to corresponding ones of said individual light source assigned thereto;
said apertures have a size and shape adapted to respective images of said individual light sources in said second plane;
said illumination optics define a first main plane (H) and a second main plane (H');
said first main plane (H) and said first plane define a first distance (s) therebetween;
said second main plane (H') and said second plane define a second distance (s') therebetween;
wherein the following relationship is satisfied for a magnification scale:

$1 \leq |s'/s| \leq 4$.

14. A method for automatically switching an illumination variant of a surgical microscope defining a viewing beam path and including an illumination device defining an illumination beam path and including: an illumination light source having mutually independently controllable individual light sources arranged in a two-dimensional array in a first plane; illumination optics defining an optical axis; said illumination optics forming a second plane conjugated with respect to said first plane; a diaphragm unit arranged in said second plane; said diaphragm unit having a plurality of apertures; said apertures being assigned to corresponding ones of said individual light source assigned thereto; a control unit; a camera arranged in said viewing beam path and connected to said control unit; and, said control unit being configured to detect a red reflex of an eye and to drive said individual light sources arranged in said two-dimensional array in dependence on a dimension figure for said red reflex, the method comprising the steps of:

recording an image of an eye via the camera arranged in the viewing beam path;

evaluating the image recorded by the camera via the control unit;

detecting red reflex of the eye via the control device;

determining a dimension figure for the red reflex; and, driving the individual light sources arranged in the two-dimensional array in dependence on the dimension figure for the red reflex.

\* \* \* \* \*